US012797609B2

(12) United States Patent
Siesbye et al.

(10) Patent No.: US 12,797,609 B2
(45) Date of Patent: Nov. 17, 2026

(54) DEVICE FOR WOUND CARE

(71) Applicant: VANQUISH INNOVATION APS, København V (DK)

(72) Inventors: Valdemar Siesbye, København V (DK); Henrik Riehm Sørensen, Silkeborg (DK); Colin Darnley Mccaig, Aberdeen (GB)

(73) Assignee: VANQUISH INNOVATION APS, København V (DK)

( * ) Notice: Subject to any disclaimer, the term of this patent is extended or adjusted under 35 U.S.C. 154(b) by 732 days.

(21) Appl. No.: 17/923,219

(22) PCT Filed: May 7, 2021

(86) PCT No.: PCT/EP2021/062202

§ 371 (c)(1),
(2) Date: Nov. 3, 2022

(87) PCT Pub. No.: WO2021/224478

PCT Pub. Date: Nov. 11, 2021

(65) Prior Publication Data

US 2023/0241381 A1 Aug. 3, 2023

(30) Foreign Application Priority Data

May 7, 2020 (EP) .................................... 20173481

(51) Int. Cl.
*A61N 1/32* (2006.01)
*A61N 1/04* (2006.01)
(Continued)

(52) U.S. Cl.
CPC ........... *A61N 1/326* (2013.01); *A61N 1/0468* (2013.01); *A61N 1/36031* (2017.08);
(Continued)

(58) Field of Classification Search
CPC .. A61N 1/326; A61N 1/0468; A61N 1/36031; A61N 1/36034; A61N 1/0492; A61N 1/205; A61N 1/08; A61B 5/2415
See application file for complete search history.

(56) References Cited

U.S. PATENT DOCUMENTS 5,018,524 A 5/1991 Gu et al.
6,535,767 B1 3/2003 Kronberg
(Continued)

FOREIGN PATENT DOCUMENTS

EP 2127694 A1 * 12/2009 ............. A61N 1/044
EP 3165154 A2 5/2017
(Continued)

OTHER PUBLICATIONS

Hunckler et al., "A current affair: electrotherapy in wound healing", Journal of Multidisciplinary Healthcare, 2017, 10:179-194.
(Continued)

*Primary Examiner* — Joseph A Stoklosa
(74) *Attorney, Agent, or Firm* — James S. Keddie; Bozicevic, Field & Francis LLP

(57) ABSTRACT

The present invention relates to electro-therapy of wounds. Specifically, a device for applying electro-therapy to a wound is provided. The device of the invention is useful for treating any kind of wound, and is especially useful for facilitating the healing of chronic wounds.

20 Claims, 5 Drawing Sheets

(51) Int. Cl.
*A61N 1/36* (2006.01)
*A61N 1/20* (2006.01)

(52) U.S. Cl.
CPC ........ *A61N 1/36034* (2017.08); *A61N 1/0492* (2013.01); *A61N 1/205* (2013.01)

(56) References Cited

U.S. PATENT DOCUMENTS

| | | | |
|---|---|---|---|
| 7,016,737 B2 | 3/2006 | Petrofsky | |
| 2004/0267333 A1* | 12/2004 | Kronberg | A61N 1/36021 607/72 |
| 2005/0187591 A1 | 8/2005 | Carter et al. | |
| 2006/0129216 A1* | 6/2006 | Hastings | A61B 5/076 607/2 |
| 2006/0270942 A1 | 11/2006 | McAdams | |
| 2008/0161884 A1* | 7/2008 | Chandler | A61N 1/0468 607/148 |
| 2009/0132010 A1 | 5/2009 | Kronberg | |
| 2011/0160811 A1 | 6/2011 | Walker | |
| 2016/0081580 A1* | 3/2016 | Bergelin | A61B 5/445 600/554 |
| 2016/0103461 A1 | 4/2016 | Maruyama et al. | |
| 2016/0213521 A1* | 7/2016 | Bacon | A61F 13/0243 |
| 2017/0224990 A1* | 8/2017 | Goldwasser | A61N 1/0476 |
| 2020/0061379 A1 | 2/2020 | Bogie et al. | |

FOREIGN PATENT DOCUMENTS

| | | |
|---|---|---|
| WO | WO 02/098502 A2 | 12/2002 |
| WO | WO 2005/032652 A1 | 4/2005 |
| WO | WO 2008/013936 A1 | 1/2008 |
| WO | WO 2009/060211 A1 | 5/2009 |
| WO | WO 2014/188070 A1 | 11/2014 |
| WO | WO 2015/157725 A1 | 10/2015 |
| WO | WO 2019/156951 A1 | 8/2019 |

OTHER PUBLICATIONS

Kloth, "Electrical Stimulation Technologies for Wound Healing", Advances in Wound Care, Feb. 1, 2014, 3(2): 81-90.

Lukaski et al., "Bioelectrical Impedance Assessment of Wound Healing", Journal of Diabetes Science and Technology, Jan. 2012, 6(1): 209-212.

* cited by examiner

DEVICE FOR WOUND CARE

CROSS-REFERENCE TO RELATED APPLICATIONS

This application is a § 371 national phase of International Application No. PCT/EP2021/062202, filed on May 7, 2021, which claims the benefit of European Application No. 20173481.1, filed on May 7, 2020, which applications are incorporated by reference herein.

FIELD OF THE INVENTION

The present invention relates to electro-therapy of wounds. Specifically, a device for applying electro-therapy to a wound is provided. The device of the invention is useful for treating any kind of wound and is especially useful for facilitating the healing of complex and chronic wounds.

BACKGROUND OF THE INVENTION

Chronic wounds, such as diabetic, venous, arterial, pressure and infectious ulcers, place an immense financial cost on the healthcare system, while also causing pain and physical stress on the afflicted patients and their surroundings. The dominant way to heal chronic wounds today is to apply a bandage or wound dressing, i.e. a bandage with healing factors applied in it, in combination with antibiotic treatments to avoid or combat infection. The use of antibiotic treatments may lead to antibiotic resistance or other detrimental effects. Furthermore, such treatments are lengthy and are in many cases not particularly efficient and it may therefore take months or even years to heal chronic wounds, during which time the quality of life for the patient will be reduced. The cost for the healthcare system for these treatments are also high as many patients suffering from chronic wounds are elderly patients with compromised immune systems, for whom the wound provides a highly increased risk of infection, thus leading to further complication.

Electro-therapy has been documented to promote blood flow and accelerate wound healing, thus making it an attractive alternative or supplementary treatment. Because the treatment duration for healing wounds and promoting blood circulation require longer treatment periods for the body to respond, a preferred way of carrying out the treatment is by implementing electrodes into a wound dressing. The wound dressing is applied at the site of the wound and fastened such that the electrodes are in contact with the wound for a sustained period of time. The following electrotherapies constitute relevant examples from the art.

WO2005032652A1 relates to a dressing for treating damaged tissue, incorporating a pair of electrodes and a conductive gel between the electrodes. An electric current pass between the electrodes through the gel to repair the damaged tissue. Sensors can be incorporated into the dressing along with a control unit. The sensors are configured to detect environmental parameters, which may be one of an oxygen, pH, bacterial infection or temperature level. The control unit can adjust current supplied to the electrodes according to environmental parameters detected by the sensors. Alternatively, one or more pre-defined programs can be stored in the control unit for supplying an alternating current to the electrodes with a varying amplitude, frequency and waveform.

WO2009060211A1 relates to an apparatus providing electrical stimulation to tissue from a control unit and at least one electrode connected to the control unit. A fixation element holds the at least one electrode against the tissue and holds the control unit in a fixed position with respect to the tissue. The control unit is configured to supply electrical current to the at least one electrode for stimulation of the tissue.

WO02098502 relates to an electrode system for facilitating the healing of a wound. The device has a supporting structure, and two electrodes attached to the supporting structure. One of the electrodes surrounds the other on the supporting structure. The electrodes are applied to the wound and a voltage potential is applied across the electrodes, so that a current is caused to flow between them and through the wound.

WO2008013936 relates to an electrode system for applying therapy to a wound. The system comprises two electrodes: the first electrode is configured at least in part to be applied to the wound and the second electrode is configured at least in part to be applied to one of skin surrounding the wound and an outer portion of the wound. The system furthermore comprises one or more feedback sensors to detect the effectiveness of the treatment and adjust the electrical stimulation. The feedback sensors are connected to a control module, which can adjust the voltage based on the sensors output. The feedback sensor may be a reactive sensor, an electrochemical sensor, a biosensor, a physical property sensor, a temperature sensor, a sorption sensor, a pH sensor, a voltage sensor, a current sensor, or a combination thereof.

Considering the devices disclosed in the prior art there is still a need for an improved electro-therapy device, which facilitates faster healing of wounds.

DISCLOSURE OF THE INVENTION

In a first aspect, the present disclosure provides a device for applying electro-therapy to a wound of a mammal, the device comprising at least two stimuli electrodes, at least two sense electrodes, the stimuli electrodes and the sense electrodes being configured to be electrically in contact with skin surrounding a wound, a control module, a voltage measurement circuit, the voltage measurement circuit being in connection with the sense electrodes and being configured to communicate with the control module, and a controlled voltage source being in connection with the stimuli electrodes and being configured to communicate with the control module;

wherein the control module is configured to

- perform a frequency sweep at a calibration voltage delivered by the controlled voltage source,
- receive one or more measured voltage drops from the voltage measurement circuit, the voltage drop(s) being measured with the sense electrodes; and
- adjust the voltage outputted from the controlled voltage source, based on the measured voltage drop(s).

Consequently, the control module may control the voltage source to deliver the correct voltage for electro therapy to the wound based on a calibration process. Preferably, the calibration voltage is delivered at 0.1 Vpp-3 Vpp as an AC signal, preferably as a 1 Vpp AC signal. Preferably, the calibration process is performed prior to applying a current for electrotherapy to the wound. Preferably, the current outputted from the controlled voltage subsequent to the current with the calibration voltage is to perform electrotherapy. The current for electrotherapy is preferably outputted as pulsed mono-phasic DC current.

The frequency sweep may be performed by applying the calibration voltage at different frequencies, e.g. in steps in-between 1 Hz to 1000 kHz, preferably 10 Hz to 100 kHz.

Such a device is useful for treating any kind of wound and is especially useful for facilitating the healing of chronic wounds. Such chronic wounds may arise from a surgical infection, a diabetic infection, a surgical wound such as from a c-section, a trauma wound, a venous infection, a pressure ulcer, a venous ulcer, a diabetic foot ulcer, a diabetic foot, arterial ulcers and others.

In the context of the present disclosure, skin surrounding a wound should be understood as any area of skin adjacent to or which abuts the wound. It should also generally be understood as skin which is at maximum 50 mm from the edge of a wound.

In the context of the present disclosure, electrodes that are configured to be electrically in contact with skin surrounding a wound should be understood as electrodes which have a surface or which can be configured to have a surface suitable for being contact with skin surrounding a wound, which surface can make an electrical contact to the skin surrounding a wound. A suitable surface is substantially flat and/or may be curved or bend to a shape that has a surface fitting the curvature of the skin, as is known from patches such as band-aid or cardiac monitoring electrodes. The electrodes may have any shape, if the shape results in a suitable surface. The surface should at least in part be of conductive material, such that electricity can be conducted through the electrodes and the skin the electrodes are arranged on. To improve electrical contact, a gel layer may be arranged between the electrode and the skin.

The voltage measurement circuit may be any circuit suitable for measuring an electric potential difference, such as an analogue to digital converter, or an analogue circuit that outputs one or more logic voltage levels based on the measured value.

The current measurement circuit may be any circuit suitable for measuring a current, such as an analogue to digital converter or an analogue circuit that outputs one or more electrical signals based on the measured value.

The control module may be any circuit that can read analogue or digital inputs that encode voltage and/or current level values.

The electrodes may be of any material with good conductive properties (conductor), such as a metal such as cobber, silver, iron or led, or an alloy, or other conductive materials such as carbon.

The electrical contact between the electrodes and the skin surrounding a wound may be any kind of contact made between an electrode and the skin surrounding the wound, which enables the conduction of a current. For example, it may be a direct contact between a conductor of the electrode and the tissue. It may also be indirect, such as when a conductive medium is laid between the electrode and the skin surrounding the wound. Without limiting the present disclosure to a specific conductive medium, an example of such a conductive medium may be conductive hydrogels, which are well known from their use in electrocardiography and in ultrasound applications. The conductive medium may also be a solution of an electrolyte. For a given wound, a conductive medium may cover the skin surrounding the wound or cover a portion of the skin surrounding the wound.

The device of the present disclosure allows for a current to run through a wound, when the stimuli electrodes of the device are put into electrical contact with the skin surrounding the wound. The device supplies the current through the stimuli electrodes, and the current may run from one of the stimuli electrodes, through the skin, through the wound, through the skin again, and to another stimuli electrode. When a current is applied to the wound by the device, the electrical field formed in the wound may accelerate wound healing, and as such the device may provide electrotherapy for a wound.

Being able to apply an electrotherapy to a wound through the skin surrounding the wound is preferred over applying electrotherapy directly on the wound itself, as placing the electrodes inside or onto the wound may interfere with how wound treatments are carried out today. For example, in conventional wound care, dressings may be applied to the wound to drain the wound of moisture or many other functions. To be effective, such dressing often need to be arranged so that they are in contact with the wound itself. Arranging electrodes on, inside or onto the wound therefore hinders the access of the dressings contact to the wound and thereby the dressings effects. As the device of the present disclosure may be used for applying electrotherapy to a wound through the skin surrounding the wound, the device does not hinder the use of dressings that are arranged to be in contact with the wound itself. Hence the device of the present disclosure enables that both electrotherapy and conventional wound care may be carried out simultaneously. Arranging the electrodes on or onto skin surrounding the wound furthermore enabled easy installation of the electrodes and may afford less disruption of sore crust formation and pain for the patient when arranged and removed when compared to arranging and removing electrodes, which has been arranged on, onto or inside the wound itself.

When the stimuli electrode and the sense electrodes are arranged on skin surrounding the wound, the measured voltage drop may depend on the electrical characteristics of the wound. Hence, the device of the present disclosure further allows for a regulated electrotherapy of a wound, wherein the voltage supplied to the wound by the device has been adjusted based on a measured voltage drop dependent on the particular wound. The device may therefore adjust the voltage level to a level tailored for the particular wound being treated, wherein the resulting tailored electrotherapy may result in an improved efficacy compared to a non-tailored electrotherapy. Since both the stimuli electrode and the sense electrodes are configured for being arranged on the skin surrounding the wound, the device may be used for a regulated electrotherapy, adjusted for a particular wound, wherein the adjusted electrotherapy has been achieved without the device touching the wound itself at any point. Hence, the device of the present disclosure may be used for a regulated electrotherapy, without interrupting conventional wound care, which is supplied on, onto or inside the wound itself.

Having at least two sense electrodes allows for the device of the present disclosure to be used for measuring the voltage drop over the wound itself, through the skin. The two sense electrodes may eliminate the measurement of the unknown skin impedance and thereby measure a more accurate voltage drop across the wound. Further, a differential measurement of voltage drop may be made with the two sense electrodes, wherein common mode noise may be reduced or eliminated. As such, a more precise measurement of the voltage drop over the wound may be made using the device of the present disclosure.

The at least two sense electrodes and the at least two stimuli electrodes may be formed by the same two electrodes. The device may comprise two electrodes, each of the two electrodes being switchable between being a stimuli electrode and a sense electrode. In an embodiment where the device comprises two electrodes, the device may further comprise a multiplexer allowing for each of the two electrodes to switch between being a stimuli electrode and a sense electrode. In an embodiment where the device comprises two electrodes, the two electrodes may act as sense electrodes when performing the frequency sweep at a calibration voltage, and subsequently the two electrodes may act as stimuli electrodes delivering a current to the wound for electro-therapy.

In an embodiment, the device further comprises a current measurement circuit, the current measurement circuit being in connection with the stimuli electrodes and being configured to communicate with the control module, and wherein the control module is further configured to

- receive one or more measured current levels from the current measurement circuit; and
- adjust the voltage outputted from the controlled voltage source, based on the measured voltage drop(s) and the measured current level(s).

The level of current flowing through the stimuli electrodes, when the stimuli electrodes are arranged on the skin surrounding the wound depends on the electrical impedance or resistance of the wound. Hence, the device of the present disclosure may further allow for a regulated electrotherapy of a wound, wherein the voltage supplied to the wound by the device may have been adjusted based on a measurement of current, which depends on the impedance of the particular wound. Using the current measurement alone or the current measurement in combination with the measured voltage drop, the device may provide a regulated electrotherapy of a wound, wherein the voltage supplied to the wound by the device may have been adjusted to a level tailored for the particular wound being treated. The tailored electrotherapy may yield an improved wound healing efficacy relative to a non-tailored electrotherapy.

In an embodiment, the control module is further configured to calculate an impedance from one or more measured voltage drop(s) and one or more measured current level(s) and adjust the voltage output of the controlled voltage source to a level at which the voltage drop measured between the sense electrodes is in the range of 0.05V to 1V per numerical Ohm of the calculated impedance.

The voltage output may be regulated so that the voltage drop measured between the sense electrodes is in the range of 0.05V to 1V, 0.07V to 0.8V, 0.08V to 0.6V, 0.09 to 0.5V, or 0.1V to 0.4V per numerical Ohm of the calculated impedance. For instance, if the calculated impedance is 50 Ohms, the voltage output may be regulated to a level at which the voltage drop measured between the stimuli electrodes is about 10V, which is equal to 0.2V per numerical Ohm value of the calculated impedance. The inventors have, based on wound models, estimated that the impedance depends on the wound size, and that there is a relationship of roughly 0.8 Ohm per mm distance through a wound. Hence, the impedance may be used as a proxy for size of the wound, and adjusting the voltage drop over the wound based on the impedance may yield a suitable electrotherapy. The above-mentioned measured voltage drops that have been regulated according to the impedance are especially suitable for accelerating wound healing, as they may yield an approximate electrical field through the wound of 50-350 mV/mm. These levels are, without being bound by theory, thought to be especially suitable for wound healing.

In an embodiment, the controlled voltage source is configured to output DC pulses having a frequency in the range of 50 to 500 kHz.

Experiments using an AC voltage source at 2 Vpp have shown that a low effective electrical impedance of the skin may be observed when such current pulses (high frequency pulses) are applied to the skin. Such low impedance values have been observed to be in the range of 144 to 173 ohms for pulses of 50 to 500 kHz (2 to 20 μs). The same effect is thus expected for DC pulses of the same frequencies. On the contrary, impedance values of the skin are much higher when the frequency of the current pulses are lower, such as 1000 to 20,000 ohms for 1 Hz to 1 kHz. The embodiment may therefore advantageously allow a greater current flow through the skin, which, without being bound by theory, improves the therapeutic effect. In addition, the device of the present disclosure may allow for the determination of the approximated voltage drop over the wound, without having to take into account differences in the impedance in the skin surrounding the wound, which can vary greatly.

Furthermore, the experiments using the AC voltage source at 2 Vpp show that current pulses having a frequency in the range of 50 to 500 kHz are pain free, whereas pulses having a frequency of 0.8 to 3 kHz result in a direct sense of pain. The embodiment therefore advantageously allows for a pain free application of a therapeutic current and may be pain free even when applied for many hours, such as 0.5-12 hours, 0.5-8 hours, or 0.5-4 hours.

The current pulses may have a frequency in the range of 5 kHz to 500 kHz, 10 kHz to 500 kHz, 15 kHz to 400 kHz, 20 to 300 kHz, 25 to 250 kHz, or 30 to 200 kHz.

The frequency of the pulsed direct current refers to how many cycles of periods with and without voltage per second the pulsed direct current has. For instance, if the pulsed direct current has a frequency of 2 Hz, the pulsed direct current will have two periods with voltage and two periods without voltage, such as 0.25 seconds of 2V, then 0.25 seconds of 0V, then 0.25 seconds of 2V and then 0.25 seconds of 0V. The periods with or without voltage do not need to be of the same duration, and the relationship between periods with and without voltage may be in the range of 1:1.1 to 1:20, 1:1.5 to 1:10, or 1:2 to 1:5. Furthermore, the rise and fall in voltage may take any suitable form, such as a sawtooth wave, a square wave, a triangular wave, a sine wave, or a combination thereof.

In an embodiment, the voltage outputted from the controlled voltage source has a duty cycle in the range of 1-50%.

Such a duty cycle results in a suitable electrotherapy of a wound, especially in combination with the DC pulses disclosed in claim 5. Such a duty cycle may also prevent excessive pH build-up in the treated tissue. Without being bound by theory, the greater the duty cycle (as in increasing % duty cycle), the greater the wound healing effect is, until a threshold is reached. Above the threshold, the level of power may be damaging to tissue and/or cells, the damage being caused by e.g. heat and/or pH build-up. Further, by using a duty cycle, power may be saved which increases battery life and extends total treatment time. The duty cycle may be in the range of 1-10%, 1-20%, 1-30%, 1-40%, or 1-50%.

The DC signal may be in a square-wave form (pulse width modulation, where the frequency may for instance be 10 kHz, the amplitude 10V and the duty cycle 10%). When applied to a wound, the electrical pulses may be bandlimited due to the impedances, such that the electrical signal going through the wound becomes mores sinusoidal in shape. The signal may also be intentionally band-limited, or by other means shaped such that the rise time is extended in comparison with for instance a perfect square-wave signal. The longer rise time alleviates uncomfortable sensations, which arise from sudden electrical stimulation. The current is preferably mono pulsed DC and will for a given time, for instance 1 min to 1 hour, run in a first direction through the electrodes and the wound. After this period, the current may be applied in the opposite direction of the first current direction. The purpose of the mono pulsed DC signal is to mimic the natural electrical stimulation occurring in wounds, which may not be present or compromised in e.g. chronic wounds or other severe wound types. Without being bound by theory, it is believed that by applying the current in varying directions and thus stimulating the healing process from several wound edges during a course of treatment, the wound healing is more efficient.

In an embodiment, the device further comprises two supporting structures, wherein at least one of the stimuli electrodes and at least one of the sense electrodes are attached to each supporting structure.

The supporting structure enables easy handling of the electrodes, such that instead of having to place two or more stimuli electrodes and two or more sense electrodes at the wound site, only at least two supporting structures need to be arranged at the wound site. The supporting structure is suitably of any material which is suitable for disposable use, such as plastics, fabrics, paper or a combination thereof.

The supporting structures may have more than one stimulus electrode and more than one sense electrode connected to it. For example, one supporting structure may have two stimuli electrodes and two sense electrodes connected to it.

In an embodiment, each supporting structure has at least one of the stimuli electrodes and has at least one sense electrode located within 5 to 50 mm of the stimuli electrode.

Such arrangement of sense electrodes and stimuli electrodes allows for reliable measurements of voltage drop to be obtained on the device. The distance between sense electrode and stimuli electrode may be in the range of 50-10, 50-20, 40-10, 40-20, 30-10, or 20-10 mm.

By having the stimuli electrode in close proximity of the sense electrode by default, the installation of electrodes becomes less complicated for the health care professional. For instance, the health care professional may place two supporting structures according to the embodiment on opposite sides of the wound on the skin surrounding the wound.

In an embodiment, at least one of the electrodes and/or, when present, at least one of the supporting structures may be one or more of cuttable by a sharp tool, foldable by hand, or tearable by hand.

Such electrodes and/or supporting structures may allow for the modification of the area of the electrodes that is intended to be facing the skin surrounding the wound. The modifications may be made to adapt the area of the electrodes, so that the area surrounds a greater portion of the wound. Without being bound by theory, the more the electrodes surround the wound, the greater the efficacy of the therapy is. It is thought that an electrode which surrounds the wound more completely may apply a current through a greater area and/or volume of the wound than an electrode only partly surrounding the wound. Additionally, electrodes and/or supporting structures that have been reduced in size to fit the wound may be handled and installed at the wound site more easily by the health care professional allowing for more wound types and shapes to be treated with the device.

The supporting structure may be foldable, so that when folded, the folded part shields one or more electrodes from electrical contact. The electrodes may also be folded against themselves, shielding the part abutting itself from electrical contact. The electrodes and/or the supporting structure may preferably be cuttable, so that a modification of the area of the electrodes that is intended to be facing the skin surrounding the wound area may be achieved by cutting. By providing a cuttable supporting structure, the modification of the area of the electrodes that is intended to be facing the skin surrounding the wound may be achieved by cutting off a part of the supporting structure onto which one or more electrodes are connected, resulting in the one or more electrodes being disconnected from the supporting structure. The electrodes and/or the supporting structure may also be suitable for being teared apart, by for instance having punctured lines or thin lines of material, allowing the electrodes and/or supporting structures to be pulled apart by hand. The materials of the supporting structure and/or the electrodes may also be thin and/or of low strength, which would allow any part of the electrode and/or supporting structure to be pulled apart by hand. The modification of the area of the electrodes that is intended to be facing the skin surrounding the wound may also be achieved by providing supporting structures and/or electrodes that are two or more of cuttable, tearable and foldable. For instance, a supporting structure could be partly cut, in order to facilitate more easy folding or tearing.

The electrodes may be arranged on the supporting structure with a spacing between them, such that the supporting structure may be cut without cutting the electrodes. Hence, any particular electrode on each supporting structure may be removed from the supporting structure by cutting only the supporting structure. The supporting structure may optionally be marked with a line (e.g. a film may be arranged on top of the supporting structure to indicate a line, or any other kind of suitable marking on the supporting structure) which indicates where the supporting structure may be cut to remove an electrode.

In an embodiment, the control module is further configured to adjust the voltage outputted from the controlled voltage source based on at least one further condition being a pre-defined distance.

Having a device configured with a pre-defined distance may allow for the electrotherapy to be adjusted according to the approximate dimensions of the wound. Such an electrotherapy may be especially suitable for the particular wound being treated. The pre-defined distance of the device may be configured in a number of ways, such as via buttons on the device, or wirelessly by sending a signal to the device. When stimuli electrodes of a specific size are used with the device, the device may detect the size of the electrodes and thereby configure the pre-defined distance. For instance, the system may detect the impedance characteristics of the electrodes and select a pre-defined distance based on the impedance characteristics.

In an embodiment, the control module is further configured to regulate the voltage outputted from the controlled voltage source to a level at which the measured voltage drop is in the range of 30-350 mV per mm of pre-defined distance.

Hereby, an electrical field suitable for electrotherapy is obtained.

In an embodiment, the average current outputted from the controlled voltage source is limited to the range of 1 to 10 mA.

Such a current is generally not tissue damaging and results in a current suitable for electrotherapy. The device may be limited to these output levels in order to mitigate applying harmful currents to wounds. The peak current levels may be greater than e.g. 10 mA.

In an embodiment, the control module is further configured to increase the voltage outputted from the controlled voltage source from a first level to a second level.

In another embodiment, the control module is further configured to increase the voltage outputted from the controlled voltage source gradually and/or stepwise from a first level to a second level.

Immediately applying a target level of voltage to a wound may be painful/uncomfortable for the mammal or patient. Having at least two levels of voltage will be less painful/uncomfortable for the mammal, as it slows the in-flow of current to the skin/wound. More steps over longer time will mean slower inflow and potentially less pain/uncomfortableness. Hence, a device configured for applying voltage levels in steps or gradually provides a less painful or less uncomfortable electro-therapy.

In an embodiment, the control module is further configured to wirelessly communicate to an external unit one or more measured voltage drop values and one or more of the measured current levels, and/or one or more impedance values calculated from one or more measured voltage drop values and one or more of the measured current levels.

The external unit may be any suitable device for receiving data via a wireless protocol, such as a smartphone or a computer.

Such a wireless communication may be used by a patient and/or a healthcare professional to monitor the status of the wound of the patient, without having to remove bandages, wound dressing or other items arranged at or fixed to the wound site. As an example, the wireless communication may be data transmittal e.g. through a Bluetooth protocol from the device of the present disclosure to an external unit, such as a smartphone, a hand-held electronic device, or a computer. The external unit may use the received data to calculate an impedance value of the wound or it may receive an impedance value from the from the device of the present disclosure. The impedance value is an indicator of the wound size, as the smaller the value is, the smaller the wound is.

In an embodiment, the control module is further configured to receive instructions from the external unit via wireless communication, wherein the instructions regulate the voltage output and/or the current output of the device.

Advantageously, such a device may be used by a patient and/or a healthcare professional to adjust the electrotherapy, without having to remove bandages, wound dressing or other items fixed to the wound site.

The electrodes may also be covered by a removable film, which abuts the electrode and/or a conductive gel arranged between the electrode and the removable film. The removable film serves the purpose of protecting the gel and/or electrode from dust. The film may also electrically insulate the conductive components of the patch. Furthermore, the film may prevent volatile components from being released from the gel, such as water evaporating from the gel. A high water content, for instance, is critical for the conductivity of a conductive hydrogel.

The control module is a device comprising any circuit and/or device suitably adapted to perform the functions described herein. The control module may comprise general purpose or proprietary programmable microprocessors, such as Digital Signal Processors (DSP), Application Specific Integrated Circuits (ASIC), Programmable Logic Arrays (PLA), Field Programmable Gate Arrays (FPGA), special-purpose electronic circuits, etc., or a combination thereof.

In an embodiment the control module is further configured to:

receive an input regarding a size of the wound adjust the voltage outputted from the controlled voltage source, based on the size of the wound.

Consequently, the control module may be calibrated based on the size of the wound. Thus, allowing for the control module to adjust the voltage outputted more precisely.

The input regarding a size of the wound may be regarding a length, a width and/or a depth of wound.

The input regarding the size of the wound may be a user inputting the dimensions of the wound to the control module. The input regarding the size of the wound may be given as one or more pictures of the wound, which may be processed by the control module to extract information regarding the size of the wound. Alternatively, the one or more pictures may be processed by an external processing unit to extract information regarding the size of the wound which may then send the extracted information to the control module, e.g. if the picture is obtained by a smart device, the smart device may firstly process the obtained pictures, or the smart device may be connected to a cloud capable of processing the images and returning the relevant information to the smart device.

The input regarding the size of the wound may be inputted directly to the control module, e.g. the control module being provided with a user interface allowing the user to give the input regarding the size of the wound directly to the control module via the user interface. The input regarding the size of the wound may be inputted to an external device communicatively connected to the control module which may then send the input regarding the size of the wound to the control module.

The device may use the input regarding the size of the wound during a calibration process, wherein the device both uses measured voltage drop(s) and the size of the wound to adjust the voltage outputted from the controlled voltage source.

In an embodiment the at least two sense electrodes and/or the at least two stimuli electrodes comprises a plurality of markers with a known dimension.

Consequently, an image may be obtained of the wound together with the plurality of markers and processed which allows for precise estimation of the size and curvature of the wound. The control module may be configured to receive an image of the wound together with the plurality of markers, and to process the image to obtain information regarding a size of the wound. Alternatively, the known markers may be compared directly to the wound to obtain information regarding a size of the wound, the comparison may then be inputted to the control module, e.g. if the wound has a width or a length equal a number of markers.

The markers may be in the shape of triangles, circles, rectangles, etc. where one or more dimensions of the markers are known.

In an embodiment the control module is further configured to:

apply the voltage outputted from the controlled voltage source in a first plurality of treatment cycles, wherein each treatment cycle comprises a treatment time period wherein the control module is configured to apply the voltage outputted from the controlled voltage source to the wound, and a down time period wherein the control module is configured to stop the voltage outputted from the controlled voltage source.

Consequently, by applying the voltage in a first plurality of treatment cycles the power consumption of the device may be reduced during electro therapy, furthermore, it allows cells to recuperate in-between treatment time periods. The reduction in power consumption may especially be advantageous if the device for applying electro-therapy is battery powered and comprises a battery, as the battery time of the device may be extended.

Preferably, the first plurality of treatment cycles is performed subsequent to the frequency sweep performed by the control module, i.e. to allow the first plurality of treatment cycles to be calibrated.

The first plurality of treatment cycles may comprise, 2, 3, 4, 5, 6 or more treatment cycles.

The treatment time period may be 5 minutes-10 hours, 5 minutes-5 hours, 5 minutes-1 hour, 15 minutes-45 minutes, or 20 minutes-40 minutes, e.g. 30 minutes. The treatment time period being a period of time where a current for electrotherapy is applied to the wound. The current applied to the wound may be a monophasic pulsed DC current or similar.

The down time period may be 5 minutes-10 hours, 5 minutes-5 hours, 5 minutes-1 hour, 15 minutes-45 minutes, or 20 minutes-40 minutes, e.g. 30 minutes. The down time period may have the same duration as the treatment time period. The down time period being a period of time where no current for electro therapy is applied to the wound.

The control module may be configured to apply a constant voltage to wound during the treatment time period, i.e. control the controlled voltage source to output a constant voltage during the treatment time period.

For example, the first plurality of treatment cycles may consist of four cycles, where the treatment time period is 30 minutes and the down time period is 30 minutes.

In an embodiment the control module is further configured to:

apply the voltage outputted from the controlled voltage source to the wound in a first plurality of treatment cycles and subsequently apply the voltage outputted from the controlled voltage source to the wound in a second plurality of treatment cycles, wherein a polarity of the voltage outputted from the controlled voltage source is reversed from the first plurality of treatment cycles to the second plurality of treatment cycles.

The applicant has found the healing of the wound is affected by the direction of the flow of current, with areas where the flow of current enters experiencing a larger degree of healing, consequently by reversing the polarity pf current, it may assure the wound undergoing electro-therapy heals uniformly.

In the context of the present disclosure, the polarity of the voltage determines a direction of the current through the wound, i.e. the direction of current from one stimuli electro to the other stimuli electrode. Thus, when the polarity is reversed current flows in the opposite direction.

Each treatment cycle within the first plurality of treatment cycles and the second plurality of treatment cycles may comprise a treatment time period wherein the control module is configured to apply the voltage outputted from the controlled voltage source to the wound, and a down time period wherein the control module is configured to stop the voltage outputted from the controlled voltage source.

The second plurality of treatment cycles may comprise, 2, 3, 4, 5, 6 or more treatment cycles.

For example, the first plurality of treatment cycles may consist of four cycles, where the treatment time period is 30 minutes and the down time period is 30 minutes, and the second plurality of treatment cycles may consist of four cycles, where the treatment time period is 30 minutes and the down time period is 30 minutes, however the polarity of a voltage applied by the voltage source being reversed during the second plurality of treatment cycles relative to the first plurality of treatment cycles.

There may be a pause in treatment between the first plurality of treatment cycles and the second plurality of treatment cycles. The pause may be 5 minutes-60 minutes, preferably 15 minutes-45 minutes, and even more preferred 20 minutes-40 minutes, e.g. 30 minutes.

In embodiments wherein the control module is configured to apply voltage to the wound in treatments cycles, before each treatment cycle the control module may be further configured to:

perform a frequency sweep at a calibration voltage to determine an impedance of the wound receive one or more measured voltage drops from the voltage measurement circuit, the voltage drop(s) being measured with the sense electrodes; and adjust the voltage outputted from the controlled voltage source, based on the measured voltage drop(s).

Consequently, change in the wound, device, skin or ambient conditions is considered at the start of each treatment cycle, and the optimal amount of voltage may be delivered to the wound.

The device for applying electro-therapy may further comprise one or more external sensors. The one or more external sensors may be communicatively connectable to the control module. The control module may be configured to generate a feedback based on sensor data received from the one or more external sensors. The feedback may be a visual feedback, e.g. if the control module is provided with a display, the control module may display the sensor data, alternatively, the control module may generate an instruction for an external device to display the sensor data. The feedback may be given via an application on a smart phone. The feedback may be a tactile feedback, e.g. if the control module is provided with a vibration device, the feedback may be provided in the form of vibrations, alternatively, the control module may generate an instruction for an external device to vibrate. The one or more external sensor may allow a user to monitor ambient conditions and try to adjust the ambient conditions to achieve optimal wound healing, e.g. it is well known that temperature has a big influence on wound healing, consequently, by being able to determine the ambient temperature via one or more external sensors, a user may adjust the ambient temperature, by moving to a different location or by changing the setting on an air condition system.

The external sensor may be a pulse, blood flow and/or blood oxygen sensor for collecting sensor data regarding pulse, blood flow and/or blood oxygen from skin surrounding the wound. The control module may be provided with a display configured to display sensor data regarding pulse, blood flow and/or blood oxygen from skin surrounding the wound. The pulse, blood flow and/or blood oxygen sensor may be integrated into the stimuli electrodes and/or the sense electrodes.

The external sensor may be a temperature sensor for collecting sensor data regarding an ambient temperature in the vicinity of the wound. The control module may be provided with a display configured to display sensor data regarding temperature. The temperature may be displayed via an application on a smart phone. The control module may have a pre-set range defining an optimal range of temperatures for wound healing, wherein if the control module determines that an ambient temperature is outside the pre-set range it generates a feedback, e.g. in the form of a warning message to be displayed or a tactile feedback. The temperature sensor may be integrated into the control module.

The external sensor may be an accelerometer for collecting sensor data regarding movement of the device.

The external sensor may be a clock for determining the time of day. The control module may be provided with a display configured to display the time of day. The control module may have one or more pre-set ranges defining an optimal time of day for wound healing and for down time, i.e. when no current is applied to the wound. The control module may be configured to determine that the optimal time of day for wound healing has been reached and generate a feedback, e.g. in the form of message to be displayed or a tactile feedback, notifying a user to start the device.

BRIEF DESCRIPTION OF THE FIGURES

In the following, embodiments of the present invention will be described with reference to the enclosed non-binding drawings.

DETAILED DESCRIPTION OF THE INVENTION

The present invention will be described below relative to specific embodiments. Those skilled in the art will appreciate that the present invention may be implemented in a number of different applications and embodiments and is not specifically limited in its application to the particular embodiment depicted herein.

Figure 1:
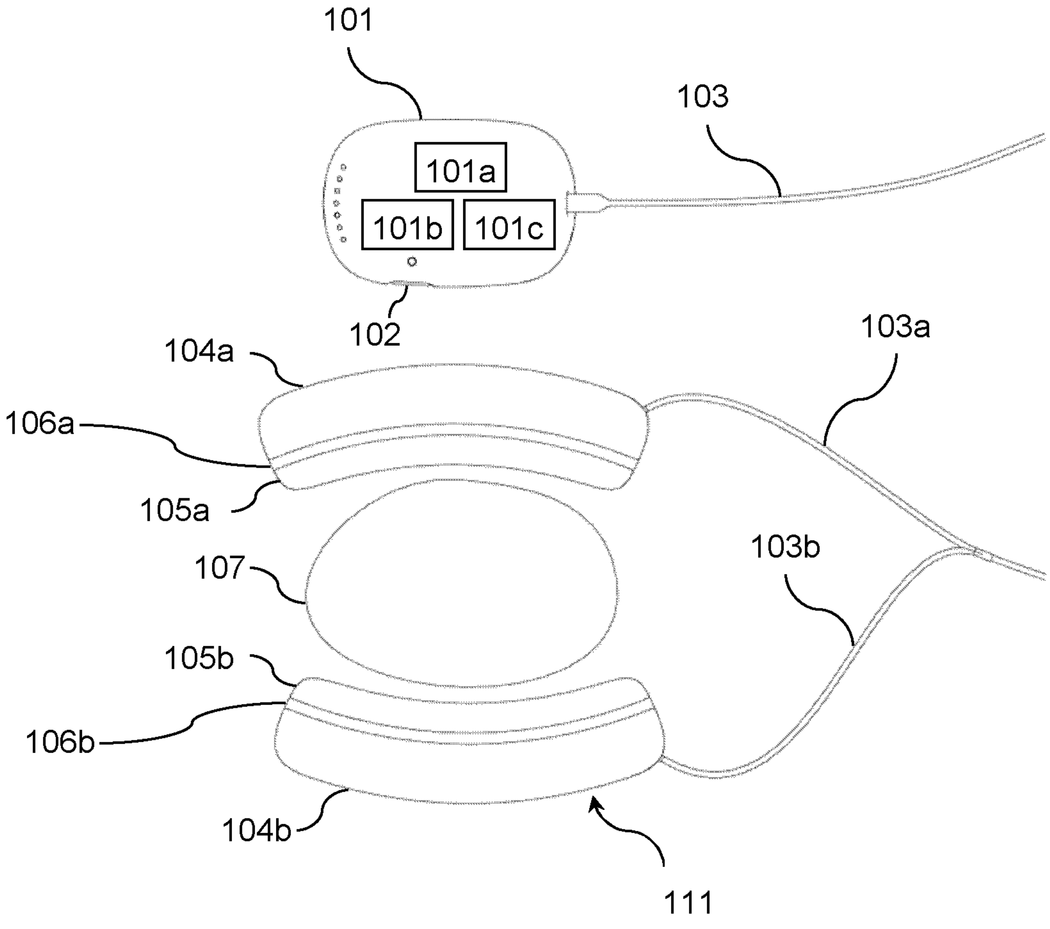
FIG. 1 shows an embodiment of the device according to the present disclosure, wherein the electrodes of the device are arranged on the skin surrounding a wound.

In general, the device of the invention is intended to be portable and fastened to a mammal or patient when in use, such that the mammal or patient may move about while electro-therapy is ongoing. In FIG. 1 is shown an example of how the device of the present disclosure may be installed at the wound site of a patient. A central unit 101 comprising a control module 101*a*, a voltage measurement circuit 101*b*, and a current measurement circuit 101*c*, is arranged close to a wound 107 and is connected via a cable 103 to two stimuli electrodes 104*a* and 104*b* and two sense electrodes 105*a* and 105*b*. The cable 103 splits into two cables 103*a* and 103*b*, each connected to a sense electrode 105*a* or 105*b* and a stimuli electrode 104*a* and 104*b* and optionally supporting structures 106*a* and 106*b*. The central unit 101 may optionally be controlled from at least a button 102 on the central unit 101. The electrode pairs 104*a* and 105*a*, and 104*b* and 105*b* are each respectively connected to supporting structures 106*a* and 106*b* arranged on opposite sides of the wound 107, the sense electrodes 105*a* and 105*b* being closest to the wound 107. A sense electrode 105*b*, a stimuli electrode 104*b* and a supporting structure 106*b* forms a patch 100*p*. In this figure, the supporting structures 106*a* and 106*b* are illustrated as being transparent, so as to show the configuration of the electrodes. In operation, electricity is outputted by the central unit 101 and conducted via the cables 103, 103*a*, and 103*b*, through the stimuli electrode 104*a* and 104*b*, and across the wound 107. The voltage drop across the wound 107 is measured via the sense electrodes 105*a* and 105*b* and the central unit 101 by the voltage measurement circuit. The control module 101*a* may calculate a suitable output voltage based on the measurements of voltage and current. A distance, such as the diameter of the wound, may be entered using the button 102, or by a wireless interface (not shown). The entered value can be used by the central unit 101 to calculate suitable voltage output levels.

Figure 2:
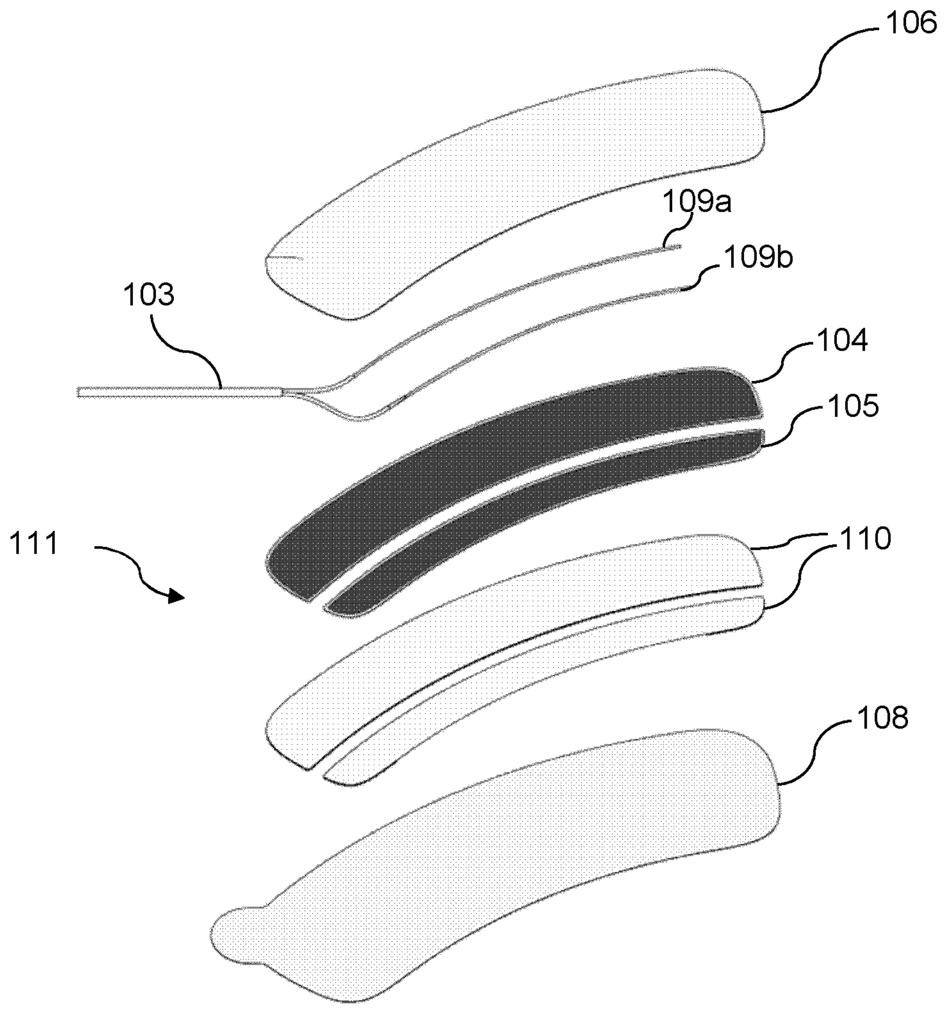
FIG. 2 shows an exploded view of a patch comprising the supporting structure and the electrodes according to the present disclosure.

FIG. 2 shows an embodiment of the invention, wherein a supporting structure 106 and electrodes 104 and 105 comprise components of a patch 111, wherein the patch 111 is shown in an exploded view. A cable 103 comprises two wires 109*a* and 109*b*, that are unshielded. When the patch 111 is assembled, the two wires 109*a* and 109*b* are respectively in electrical contact with a stimuli electrode 104 and a sense electrode 105 and are sandwiched between the supporting structure 106 and the electrodes 104 and 105. A conductive gel layer 110 may optionally be located between each respective electrode 104 and 105 and the gel layer 110 may optionally be covered by a removable film 108.

Figure 3:
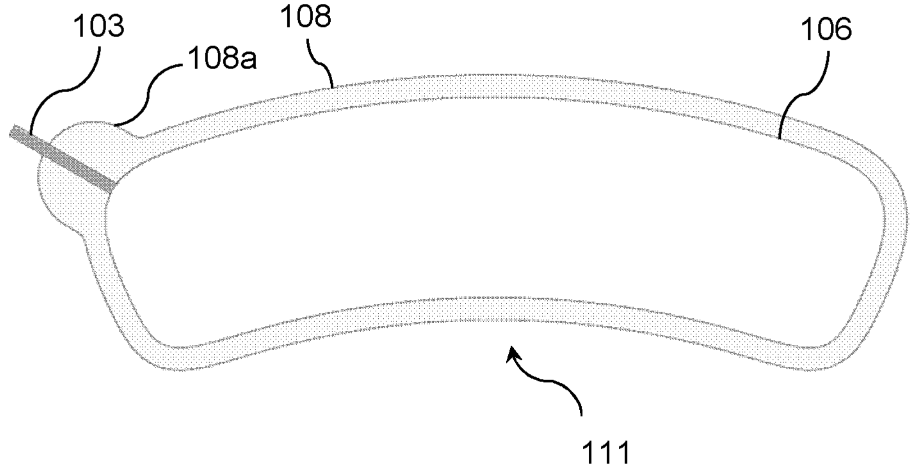
FIG. 3 shows the patch of FIG. 2 in an assembled condition.

FIG. 3 shows the patch of FIG. 2 in an assembled form. The removable film 108 optionally has a notch 108*a* to enable easy removal of the film. This embodiment may optionally be cut, for instance, across the width of the patch, such that the length of the patch is reduced. Ideally, the length of the patch is cut, so that it fits roughly with the dimensions of skin surrounding the wound to be treated.

Figure 4:
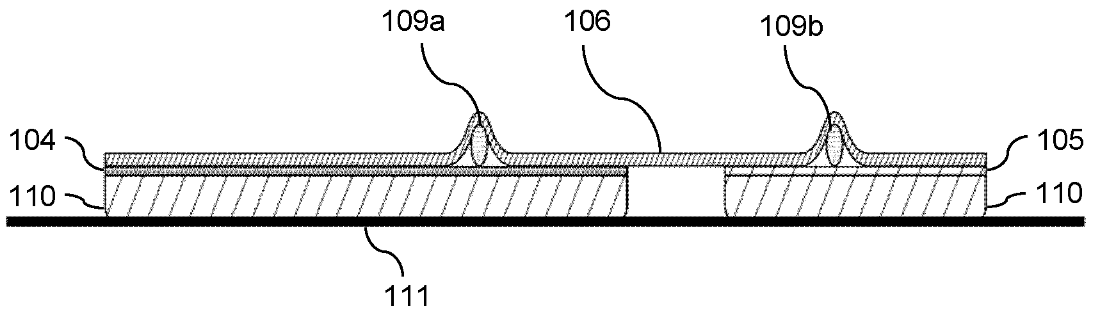
FIG. 4 shows a planar cross-section of the patch of FIGS. 2 and 3, when applied to skin.

FIG. 4 shows a planar cross-section of the patch of FIGS. 2 and 3 in an assembled form, where the removable film 108 has been removed, and the conductive gel layer 110 is contacting the surface of the skin 111 surrounding the wound (not shown).

Figure 5:
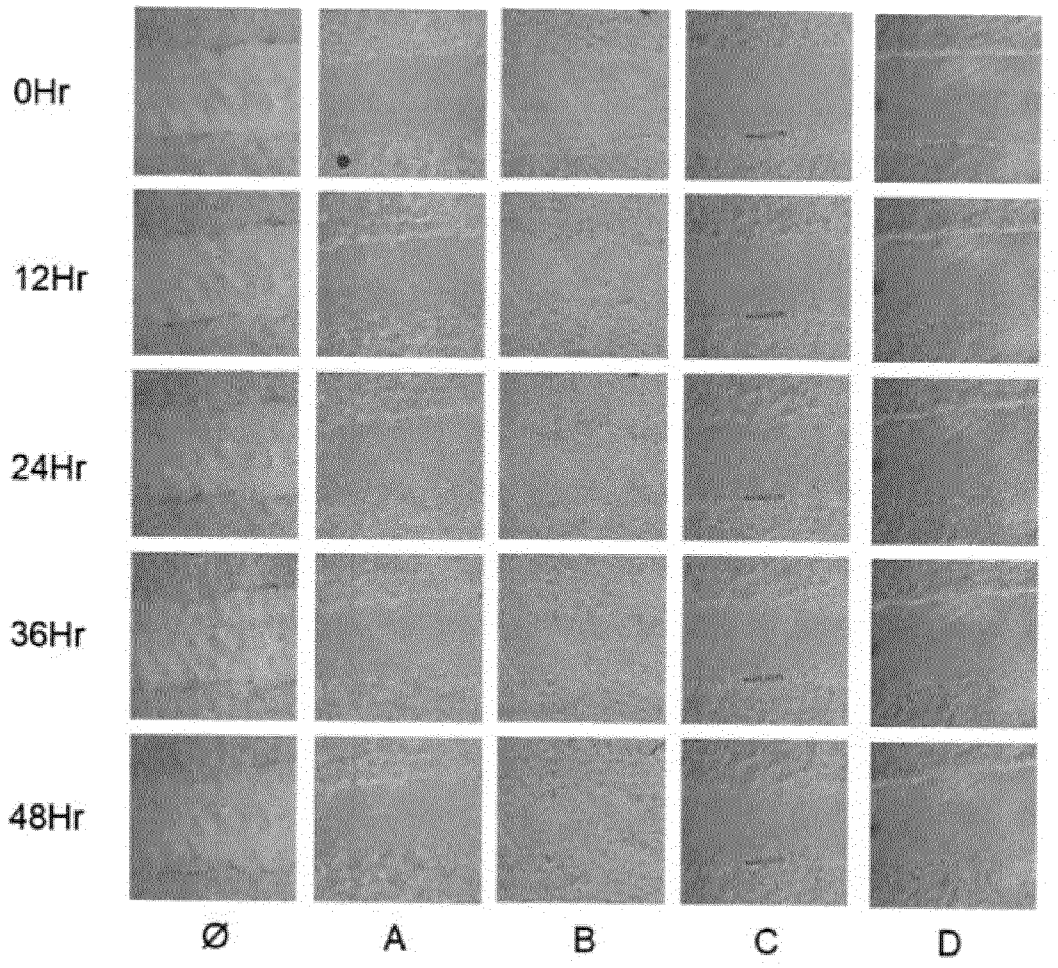
FIG. 5 shows representative light microscope images of scratch assays in monolayers of HaCaT cells exposed to electrical stimulation over 48 hours.

FIG. 5 shows representative light microscope images of the scratch assay described in Example 2 in which monolayer HaCaT cells were exposed to electrical stimulation under different conditions over 48 hours. The different conditions tested were A, pulse frequency of 0 kHz, duty cycle of 100% and electric field of 200 mV/mm; B, pulse frequency of 100 kHz, duty cycle of 2% and electric field of 200 mV/mm; C, pulse frequency of 100 kHz, duty cycle of 4% and electric field of 200 mV/mm; and D, pulse frequency of 100 kHz, duty cycle of 10% and electric field of 150 mV/mm. The control ∅ represents untreated, i.e. unstimulated, cells. Each condition was tested in triplicates and the images shown in FIG. 5 represents a representative image of the general cell behaviour observed for each condition. Images were acquired after 0 hours, 12 hours, 24 hours, 36 hours and 48 hours of electrostimulation. For all conditions, the electrical stimulation was orthogonal (top to bottom) to the scratches, the scratches being present in the middle of the image. For the control group ∅, the cell-free area, i.e. the scratch, in the middle of the image has the same size over the entire 48 hours. For conditions C and D, the cellfree area in the middle of the images shows only slight reduction in size, i.e. wound healing under these conditions were slow and less efficient. For condition A, a visible change in the size of the cell-free area was observed over the course of treatment. Cells treated with condition B by far showed the largest reduction in the size of the cell-free area, thus representing the best condition for wound healing. The healing properties of conditions A and B are shown more clearly in FIG. 6.

Figure 6:
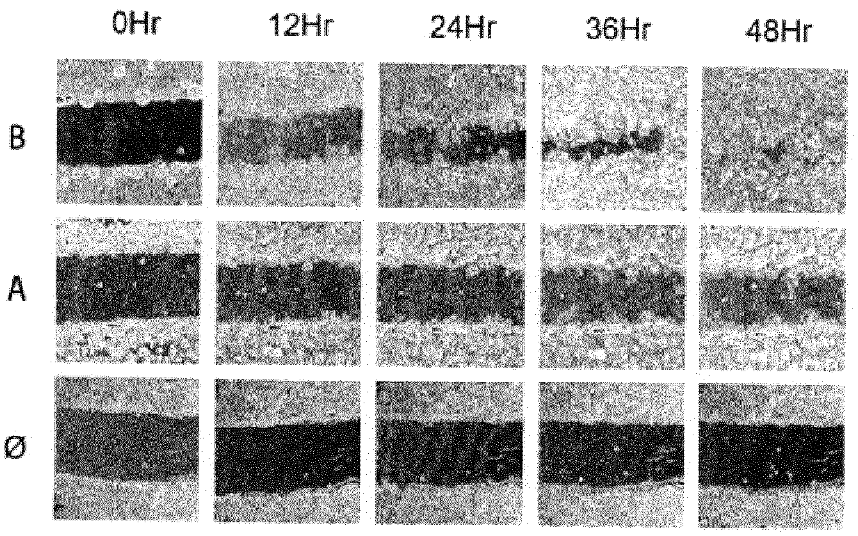
FIG. 6 shows representative light microscope images of scratch assays in monolayers of HaCaT cells exposed to electrical stimulation over 48 hours.

FIG. 6 shows representative light microscope images of the scratch assay described in Example 2 with monolayer HaCaT cells exposed to electrical stimulation under stimulated conditions (A and B) and unstimulated condition (Ø) over 48 hours. The scratch area or cell-free area represents the wound and is seen in the middle of the image as a darker area. During electrical stimulation, the size of the cell-free area is reduced in the treated cells (A and B), whereas for the unstimulated cells (Ø) this area remains unchanged in size. Furthermore, the cells treated under condition B (pulse frequency of 100 kHz, duty cycle of 2% and electric field of 200 mV/mm) display the fastest and most efficient wound healing as shown from the substantial reduction in the cell-free area which is visible already after 24 hours. After 48 hours of treatment under condition B, the cell-free area is almost completely reduced. Condition A displays a slower and less pronounced wound healing.

Figure 7:
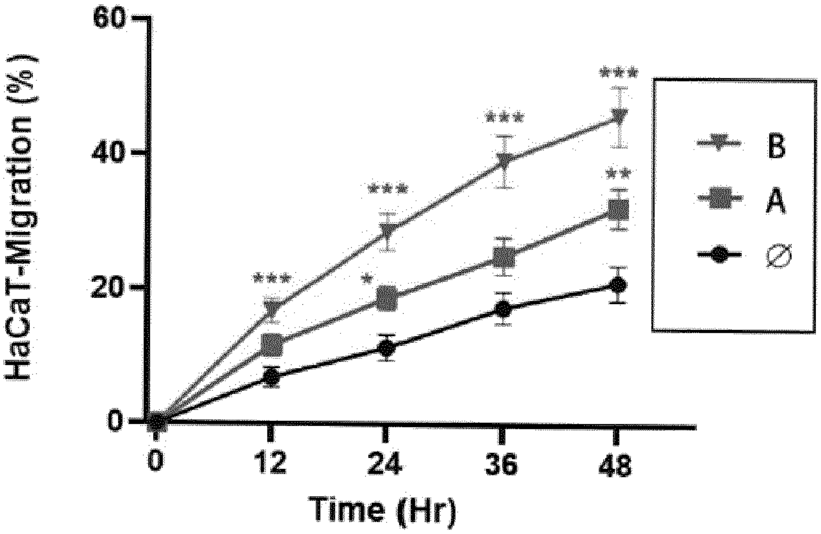
FIG. 7 shows a graph of cell migration ability of HaCaT cells exposed to electrical stimulation over 48 hours.

FIG. 7 shows a graph of the cell migration ability of HaCaT cells treated with conditions A (solid line with squares) and B (solid line with triangles) and for untreated cells Ø (solid line with circles). The graph depicts the change in cell-free area over time, which is calculated using the Image J software, an open-source image processing program used to assess wound closure by tracing the wound perimeter and calculating percentage closure. The width of the scratches at 0 hours is 100%. As seen in FIG. 7, the change in cell-free area over time, i.e. rate of wound healing, is highest for HaCaT cells treated under condition B, which is evident from the approximately 50% change in cell-free area at 48 hours.

EXAMPLES

Example 1: Demonstration of Low Impedance and No Pain at High AC Frequencies in a Simulated Wound Two electrodes were arranged on dry skin on a person's arm, the distance between the electrodes being 50 mm. The electrodes were connected in series to a signal generator with a 50 ohm output impedance. A 100 ohms resistor was inserted in series into the circuit as a measurement resistor for current measurements. A simulated wound was made on the arm by applying a thick layer of Cefar Electrogel to the skin between the electrodes. The Cefar Electrogel was applied on the skin to form a roughly circular gel layer, the gel layer being about 5 mm from each of the electrode's edges. Electrical measurements were made by connecting an oscillometer in series, the first and the second lead of the oscillometer being respectively connected right before and after the 100 ohms resistor. Briefly, the measurements showed that the AC resistance of the simulated wound is strongly frequency dependent and ranges from about 20 kOhm at 1 Hz to <150 Ohm in the range 100 kHz to 1 MHz, and that it has a DC resistance which is voltage dependent and is in the range of 40 kOhm (at 20V) to 263 kOhm (at 1V). After several hours of AC measurements, there is no irritation to the skin, while the DC (non-pulsed) measurements, which took only 10 minutes, and which measured currents below 0.5 mA, nevertheless resulted in red and irritated skin under the positive electrode, as well as some discomfort in the skin already at DC voltage/currents above 15V/150 μA. At AC frequencies of 0.8 to 3 kHz, direct sensation of pain could be felt. Below in table 1 are given impedance values of the simulated wound at different AC frequencies. The table also shows the AC frequencies at which a direct sense of pain is felt.

TABLE 1

| AC Frequency [kHz] | Impedance in model wound (ohms) | Pain |
|---|---|---|
| 0.001 | 19850 | NO |
| 0.01 | 16517 | NO |
| 0.02 | 15235 | NO |
| 0.03 | 12350 | NO |
| 0.04 | 9850 | NO |
| 0.05 | 8941 | NO |
| 0.06 | 8183 | NO |
| 0.07 | 7850 | NO |
| 0.08 | 7257 | NO |
| 0.09 | 6517 | NO |
| 0.1 | 6302 | NO |
| 0.2 | 3696 | NO |
| 0.3 | 2667 | NO |
| 0.4 | 1978 | NO |
| 0.5 | 1719 | NO |
| 0.6 | 1463 | NO |
| 0.7 | 1201 | NO |
| 0.8 | 1116 | YES |
| 0.9 | 1013 | YES |
| 1 | 986 | YES |
| 2 | 554 | YES |
| 3 | 425 | YES |
| 4 | 360 | NO |
| 5 | 326 | NO |
| 6 | 300 | NO |
| 7 | 281 | NO |
| 8 | 263 | NO |
| 9 | 260 | NO |
| 10 | 247 | NO |
| 20 | 205 | NO |
| 30 | 192 | NO |
| 40 | 181 | NO |
| 50 | 173 | NO |
| 60 | 166 | NO |
| 70 | 163 | NO |
| 80 | 163 | NO |
| 90 | 159 | NO |
| 100 | 155 | NO |
| 200 | 148 | NO |
| 300 | 148 | NO |
| 400 | 144 | NO |
| 500 | 144 | NO |
| 600 | 144 | NO |
| 700 | 144 | NO |
| 800 | 144 | NO |
| 900 | 144 | NO |
| 1000 | 144 | NO |
| 2000 | 153 | NO |
| 3000 | 190 | NO |
| 4000 | 263 | NO |
| 5000 | 192 | NO |
| 6000 | 218 | NO |
| 7000 | 250 | NO |
| 8000 | 200 | NO |
| 9000 | 188 | NO |
| 10000 | 188 | NO |

Conclusion: levels of current and voltage suitable for electrotherapy may be provided painlessly to a simulated wound through the skin using an AC signal having a frequency of at least 10 kHz. Pulsed DC signals similar to the AC signals are expected to generally behave in similar way and may therefore also be used in electrotherapy.

Example 2: In Vitro Studies on HaCaT Cells Stimulated Electrically Versus Control The Electrical Stimulation System Setup For the basic principle of the electrical stimulation system, the protocol published by Song et al. in 2007 (doi:

10.1038/nprot.2007.205) was used as a starting point. The key parts of the stimulation system included cell culture dishes with special structures, including cell culture chambers, salt bridges to transport the electrons, electrical stimulation devices to generate the electrical current, and scaffolding to hold everything in place. The purpose of this setup was to generate the target electric field in the cell culture environment. The protocol of Song et al. 2007 was adapted to accommodate the special requirements of the study, which included long duration of electrical stimulation, microscopic examination, etc.

Cell Culturing and Method of Scratch Assay

The HaCaT cells were cultivated in monolayers in thin chambers to avoid cell damage caused by excessive heating of the medium by the electric field. The cells were seeded in the middle of the custom-made petri dishes. Normally, the culture concentration of HaCaT cells is $1\times10^4/cm^2$. To make the cells confluent as quickly as possible in a limited space, the concentration of the cell suspension used for seeding was $95\times10^4/cm^2$. Viability of the cells under the provided experimental conditions were confirmed by trypan blue staining to be greater than 95%.

Normally, the cell-free area is generated by using a pipette tip to scratch a wound through the center of the Petri-dish, however, for the present experimental setup the use of tips led to issues with the edges of the scratches being irregular, the cells being easier to lift in layers around the edges and the cells at the edges of the scratches breaking. To circumvent these issues, a self-adhesive silicone tape was used instead of tips. The silicone tape was cut into strips of equal width (0.5-0.7 mm) and adhered to the cell culture area in advance. Once sufficient cell growth and cell adhesion was achieved, the tape was removed and satisfactory cell-free areas were generated.

The Effect of Electrical Stimulation on Cell Migration

To explore the effects of different modes of electrical stimulation on HaCaT cell migration, electrical signals with different parameters (Table 2) were applied to the monolayer of HaCaT cell culture. Stimulation (Conditions A, B, C, D) and no stimulation (control group ∅) was applied to a monolayer of HaCaT cell culture using Ag/AgCl electrodes connected via agar salt bridges, to prevent electrode products from entering cultures.

TABLE 2

Parameters tested on HaCaT cell culture systems

| Condition | Pulse frequency (kHz) | Duty cycle (%) | Electric field (mV/mm) |
|---|---|---|---|
| A | 0 | 100 | 200 |
| B | 100 | 2 | 200 |
| C | 100 | 4 | 200 |
| D | 100 | 10 | 150 |

The scratches or cell-free area in the culture system were photographed at 0, 12, 24, 36 and 48 hours after the start of electrical stimulation. At each time point, three photos of each cell-free area were taken (FIG. 5) and the cell-free area was calculated by Image J software. The original microscope magnification was 40×.

The following formula was used to calculate the migration rate of each group of cells at different time points to evaluate the migration ability:

$$\text{Migration Rate} = \frac{\text{Cell-free area }(0H) - \text{Cell-free area }(nH)}{\text{Cell-free area }(0H)} \times 100,$$

-continued $$n = 12, 24, 36, 48$$

Compared with the control group (∅), the migration rate of the experimental groups (A, B) showed an increasing trend (FIGS. 6 and 7). HaCaT cells cultures exposed to the electrical stimulation generated by Condition B (100 kHz, 2% duty cycle, 200 mV/mm) showed the most significant increase in migration ability, i.e. the fastest and most efficient wound healing. As seen from FIG. 6, the wound closed substantially after only 24 hours of electrical stimulation treatment and was almost completely closed by 48 hours of electrical stimulation treatment. As seen from FIG. 7, both conditions B and A markedly enhanced the rate of wound closure as compared to the control (∅). Furthermore, condition B significantly outperformed condition A (normal DC stimulation) in that condition B closed wounds roughly 50% faster (*p<0.05, p<0.01, *p<0.001).

Statistics

Results are presented as mean±standard error of mean (SEM). Each test conditions were performed three independent times (N=3) measured as triplicate or more (technical replicates, n≥3). Statistical analyses were performed using the GraphPad Prism Software (Version 8.0.2, El Camino Real, USA). Data sets were compared by the Kruskal-Wallis H test. $\alpha=0.05$ was set as the maximum type I error rate. *<0.05, <0.01, *<0.001 were used to classify P values in comparisons with the control group.

CONCLUSIONS

The cell system described in this example meets the requirements of testing cell migration ability.

Electrical stimulation provided under conditions A and B showed a trend of improving the cell migration ability, with the changes in condition B, i.e. a pulse frequency of 100 kHz, a duty cycle of 2% and an electric field of 200 mV/mm, being the most significant.

Based on the in vitro studies presented above, it is evident that the electrical stimulation as provided in accordance with the present inventive concept provides superior wound healing properties. Furthermore, in accordance with the data presented in Example 1, it is believed that the electrical stimulation conditions tested herewith cause minimum adverse effects to the patient during the electrotherapy. Thus, it is believed that an optimum stimulation algorithm consisting of high frequency pulses of at least 50 kHz or 100 kHz with a low duty cycle (<10%), results in the highest possible electrical field (EF) strength across a wound at a minimum battery power consumption and with minimum power dissipation in the skin. This maximizes battery life, establishes the desired EF of 50-200 mV/mm across the wound and fully avoids discomfort, such as itching, skin reactions or muscle activation, associated with DC or lower frequency currents through skin.

The invention claimed is:

1. A device for applying electro-therapy to a wound in the skin of a mammal, comprising at least two electrodes configured to be electrically in contact with skin adjacent to or abutting a wound at a maximum distance of 50 mm from an edge of a wound so as not to hinder the use of a dressing in contact with the wound itself, the at least two electrodes being switchable between being a stimuli electrode and a sense electrode, or the at least two electrodes comprising at least two sense electrodes and at least two stimuli electrodes, and the at least two electrodes being configured to apply a current through the wound, the device for applying electrotherapy further comprising a control module, and a voltage measurement circuit, the voltage measurement circuit being in connection with the sense electrodes and being configured to communicate with the control module, and a controlled voltage source being in connection with the stimuli electrodes and being configured to communicate with the control module;

wherein the control module is configured to perform a frequency sweep via the at least two sense electrodes at a calibration voltage delivered by the controlled voltage source, receive one or more measured voltage drops from the voltage measurement circuit, the voltage drop(s) being measured with the sense electrodes;

adjust the voltage outputted from the controlled voltage source, based on the measured voltage drop(s); and wherein the device is configured to detect the size of the electrodes and configure a pre-defined distance, and wherein the control module is further configured to adjust the voltage outputted from the controlled voltage source to a level at which the measured voltage drop is in the range of 30-350 mV per mm over the pre-defined distance.

2. The device according to claim 1, wherein the device further comprises a current measurement circuit, the current measurement circuit being in connection with the stimuli electrodes and being configured to communicate with the control module, and wherein the control module is further configured to receive one or more measured current levels from the current measurement circuit; and adjust the voltage outputted from the controlled voltage source, based on the measured voltage drop(s) and the measured current level(s).

3. The device according to claim 2, wherein the control module is further configured to calculate an impedance from one or more measured voltage drop(s) and one or more measured current level(s) and adjust the voltage output of the controlled voltage source to a level at which the voltage drop measured between the sense electrodes is in the range of 0.05V to 1V per numerical Ohm of the calculated impedance.

4. The device according to claim 1, wherein the controlled voltage source is configured to output DC pulses having a frequency in the range of 50 to 500 KHz.

5. The device according to claim 1, wherein the voltage outputted from the controlled voltage source has a duty cycle in the range of 1-10%.

6. The device according to claim 1, wherein the device further comprises two supporting structures, wherein at least one of the stimuli electrodes and at least one of the sense electrodes are attached to each supporting structure.

7. The device according to claim 1, wherein on each supporting structure at least one of the stimuli electrodes has at least one sense electrode located within 5 to 50 mm of it.

8. The device according to claim 1, wherein at least one of the electrodes and/or, when present, at least one of the supporting structures may be one or more of cuttable by a sharp tool, foldable by hand, or tearable by hand.

9. The device according to claim 1, wherein the average current outputted from the controlled voltage source is limited to the range of 1 to 10 mA.

10. The device according to claim 1, wherein the control module is further configured to increase the voltage outputted from the controlled voltage source from a first level to a second level.

11. The device according to claim 10, wherein the control module is further configured to increase the voltage outputted from the controlled voltage source gradually and/or stepwise from a first level to a second level.

12. The device according to claim 2, wherein the control module is further configured to wirelessly communicate to an external unit one or more measured voltage drop values and one or more of the measured current levels, and/or one or more impedance values calculated from one or more measured voltage drop values and one or more of the measured current levels.

13. The device according to claim 12, wherein the control module is further configured to receive instructions from the external unit via wireless communication, wherein the instructions regulate the voltage output and/or the current output of the device.

14. The device according to claim 1, wherein the control module is further configured to:

receive an input regarding a size of the wound adjust the voltage outputted from the controlled voltage source, based on the size of the wound.

15. The device according to claim 14, wherein the control module is further configured to regulate the voltage outputted from the controlled voltage source to a level at which the measured voltage drop is in the range of 30-350 mV per mm.

16. The device according to claim 1, wherein the at least two sense electrodes and/or the at least two stimuli electrodes comprises a plurality of markers with a known dimension.

17. The device according to claim 1, wherein the control module is further configured to:

apply the voltage outputted from the controlled voltage source in a first plurality of treatment cycles, wherein each treatment cycle comprises a treatment time period wherein the control module is configured to apply the voltage outputted from the controlled voltage source to the wound, and a down time period wherein the control module is configured to stop the voltage outputted from the controlled voltage source.

18. The device according to claim 17, wherein the control module is further configured to:

apply the voltage outputted from the controlled voltage source to the wound in a first plurality of treatment cycles and subsequently apply the voltage outputted from the controlled voltage source to the wound in a second plurality of treatment cycles, wherein a polarity of the voltage outputted from the controlled voltage source is reversed from the first plurality of treatment cycles to the second plurality of treatment cycles.

19. The device according to claim 17, wherein before each treatment cycle the control module may be further configured to:

perform a frequency sweep at a calibration voltage delivered by the controlled voltage source to determine an impedance of the wound, receive one or more measured voltage drops from the voltage measurement circuit, the voltage drop(s) being measured with the sense electrodes; and adjust the voltage outputted from the controlled voltage source, based on the measured voltage drop(s).

20. A method for applying electro-therapy to a wound of a mammal, comprising applying a device of claim 1 to the mammal;

performing a frequency sweep via the at least two sense electrodes at a calibration voltage delivered by the controlled voltage source, receiving one or more measured voltage drops from the voltage measurement circuit, the voltage drop(s) being measured with the sense electrodes; and adjusting the voltage outputted from the controlled voltage source, based on the measured voltage drop(s).

* * * * *